(12) United States Patent
Kantor et al.

(10) Patent No.: US 7,323,008 B2
(45) Date of Patent: Jan. 29, 2008

(54) FLEXIBLE STENT

(75) Inventors: John D. Kantor, Santa Rosa, CA (US); Ryan Alexander Jones, Higley, AZ (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 476 days.

(21) Appl. No.: 10/913,462

(22) Filed: Aug. 9, 2004

(65) Prior Publication Data

US 2006/0030932 A1 Feb. 9, 2006

(51) Int. Cl.
*A61F 2/06* (2006.01)
(52) U.S. Cl. ..................................... 623/1.15
(58) Field of Classification Search ....... 623/1.11–1.16
See application file for complete search history.

(56) References Cited

U.S. PATENT DOCUMENTS

| | | | |
|---|---|---|---|
| 4,886,062 A | 12/1989 | Wiktor | |
| 5,035,706 A | 7/1991 | Gianturco et al. | |
| 6,344,053 B1 | 2/2002 | Boneau | |
| 6,387,122 B1 | 5/2002 | Cragg | |
| 6,475,237 B2 | 11/2002 | Drasler et al. | |
| 6,565,599 B1 | 5/2003 | Hong et al. | |
| 2002/0111671 A1 | 8/2002 | Stenzel | |
| 2002/0120327 A1* | 8/2002 | Cox et al. ................. | 623/1.16 |
| 2004/0236406 A1* | 11/2004 | Gregorich ................. | 623/1.16 |
| 2005/0090892 A1* | 4/2005 | DePalma ................... | 623/1.13 |
| 2006/0111772 A1* | 5/2006 | White et al. .............. | 623/1.15 |
| 2006/0195175 A1* | 8/2006 | Bregulla .................... | 623/1.15 |
| 2006/0287706 A1* | 12/2006 | Olsen et al. ............... | 623/1.15 |

FOREIGN PATENT DOCUMENTS

| | | |
|---|---|---|
| WO | WO 97/49353 | 12/1997 |
| WO | WO 00/15151 | 3/2000 |
| WO | WO 2005/018500 | 3/2005 |

* cited by examiner

*Primary Examiner*—Suzette Gherbi

(57) ABSTRACT

A stent device including a stent body having a plurality of adjacent rows and one or more interconnections or interlocking rings between rows. The interconnections have first and second connecting portions with first ends permanently and immovably coupled to the rows and second ends interlocked with each other, such that the second ends of each portion can move independently of the other. The interconnections include ball and socket joints, hinge joints or universal joints. Interlocking rings have indentations for receiving the other ring, such that when interlocked, the rings will lay flat against a body lumen wall.

23 Claims, 10 Drawing Sheets

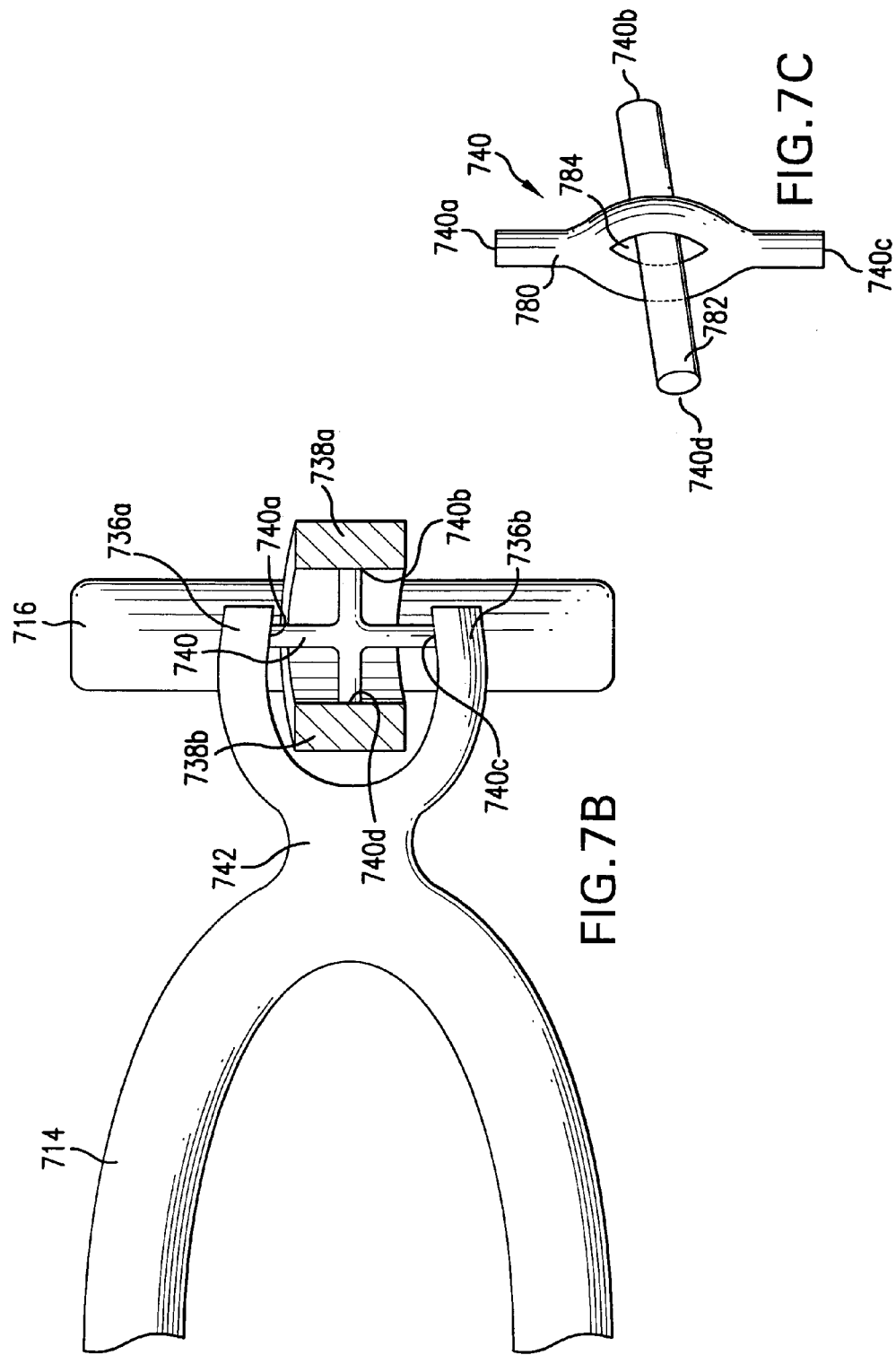

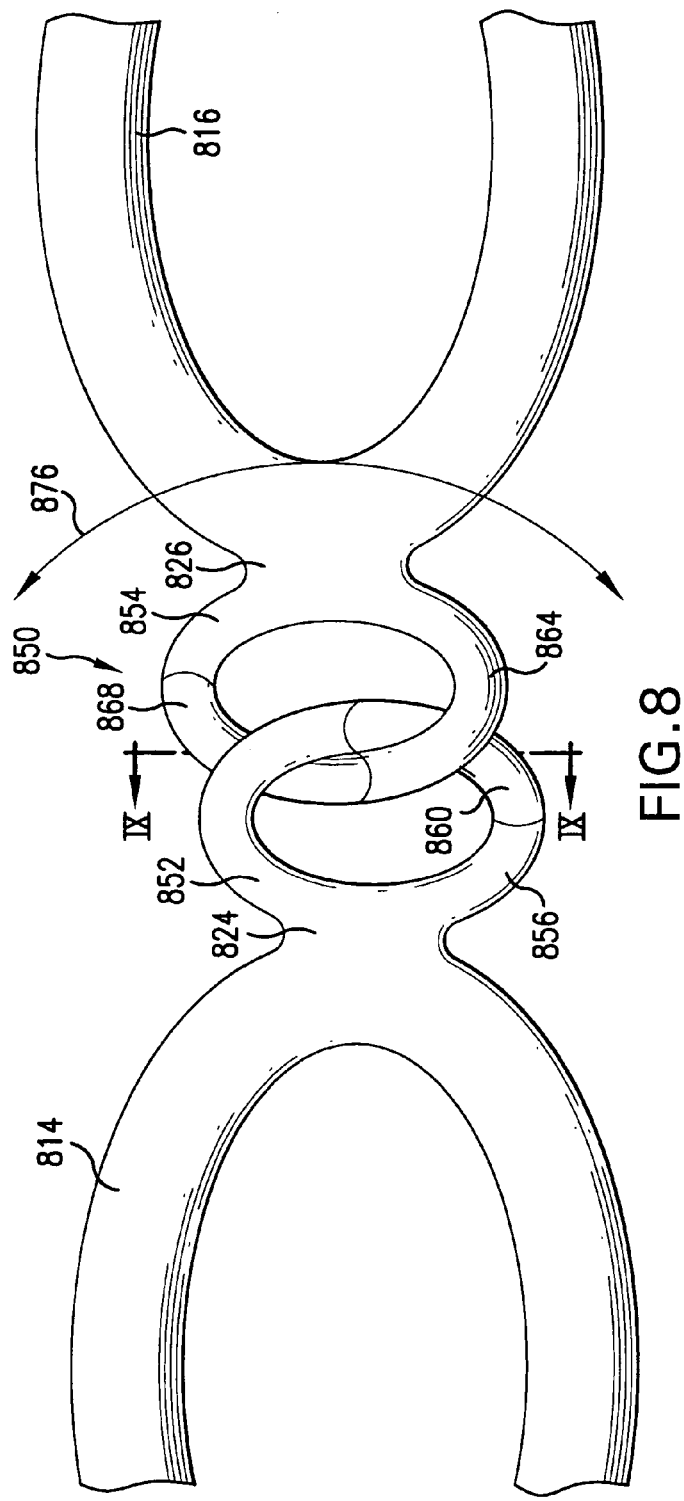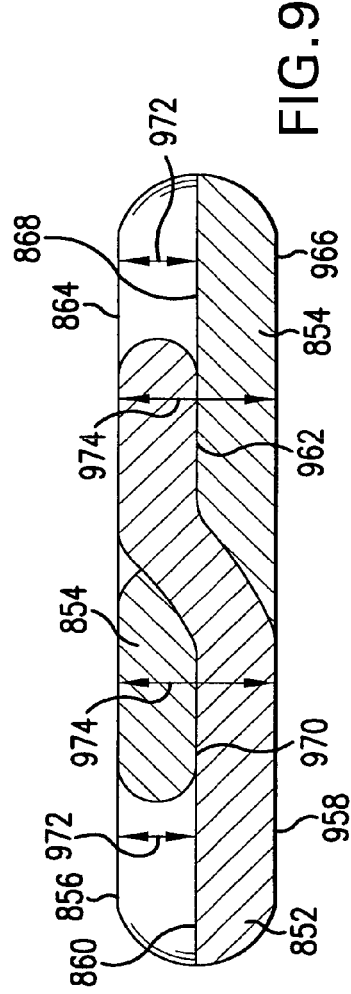
FIG.8
FIG.9

FLEXIBLE STENT

FIELD OF THE INVENTION

This invention relates generally to a medical device. More specifically, the invention relates to an implantable stent prosthesis for treatment of stenosis in blood vessels

BACKGROUND OF THE INVENTION

A wide range of medical treatments have been previously developed using "endoluminal prostheses," which terms are herein intended to mean medical devices which are adapted for temporary or permanent implantation within a body lumen, including both naturally occurring or artificially made lumens. Examples of lumens in which endoluminal prostheses may be implanted include, without limitation: arteries, such as those located within the coronary, mesentery, peripheral, or cerebral vasculature; veins; gastrointestinal tract; biliary tract; urethra; trachea; hepatic shunts; and fallopian tubes. Various types of endoluminal prostheses have also been developed, each providing a uniquely beneficial structure to modify the mechanics of the targeted lumen wall.

For example, stent prostheses have been previously disclosed for implantation within body lumens. Various stent designs have been previously disclosed for providing artificial radial support to the wall tissue, which forms the various lumens within the body, and often more specifically within the blood vessels of the body.

Cardiovascular disease, including atherosclerosis, is the leading cause of death in the U.S. The medical community has developed a number of methods and devices for treating coronary heart disease, some of which are specifically designed to treat the complications resulting from atherosclerosis and other forms of coronary arterial narrowing.

One method for treating atherosclerosis and other forms of coronary narrowing is percutaneous transluminal coronary angioplasty, commonly referred to as "angioplasty," "PTA" or "PTCA". The objective in angioplasty is to enlarge the lumen of the affected coronary artery by radial hydraulic expansion. The procedure is accomplished by inflating a balloon of a balloon catheter within the narrowed lumen of the coronary artery. In some instances the vessel restenoses chronically, or closes down acutely, negating the positive effects of the angioplasty procedure.

To provide radial support to the treated vessel in order to prolong the positive effects of PTCA, a stent may be implanted in conjunction with the procedure. Effectively, the stent overcomes the natural tendency of the vessel walls of some patients to close back down, thereby maintaining a more normal flow of blood through that vessel than would be possible if the stent were not in place. Under this procedure, the stent may be collapsed to an insertion diameter and inserted into a body lumen at a site remote from the diseased vessel. The stent may then be delivered to the desired site of treatment within the affected lumen and deployed to its desired diameter for treatment.

Access to a treatment site is most often reached from the femoral artery. A flexible guiding catheter is inserted through a sheath into the femoral artery. The guiding catheter is advanced through the femoral artery into the iliac artery and into the ascending aorta. Further advancement of the flexible catheter involves the negotiation of an approximately 180 degree turn through the aortic arch to allow the guiding catheter to descend into the aortic cusp where entry may be gained to either the left or the right coronary artery, as desired. Because the procedure requires insertion of the stent at a site remote from the site of treatment, the device must be guided through the potentially tortuous conduit of the body lumen to the treatment site. Therefore, the stent must be capable of being reduced to a small insertion diameter and must be very flexible.

One particularly flexible stent is available from the assignee of the present invention, Medtronic Vascular, Inc., and is known as the S7 STENT (shown generally as stent 101 in FIG. 1A). The S7 STENT has several rows of cylindrical segments, in this case sinusoidally shaped segments 102, which are welded together at the apexes 104 of adjacent segments. FIG. 1A shows stent 101 crimped onto an expandable balloon 106. Alternatively, the stent may be made of superelastic material such that it is positioned in a compressed state and naturally expanded within a body lumen. The shape of the sinusoidal segments is described in U.S. Pat. No. 6,344,053 to Boneau, the disclosure of which is incorporated herein by reference in its entirety.

However, stents come in a variety of shapes and sizes. For example, stents formed from a helical winding of wire are useful for covering the walls of a stent while being particularly flexible. An example of a helical winding can be found in U.S. Pat. No. 4,886,062 to Wiktor, the disclosure of which is incorporated herein by reference in its entirety. FIG. 1B shows a stent 107 having a wire formed into a series of helical windings 108, in this case sinusoidally shaped helical windings 108. The windings 108 form rows along the length of the stent 107. Just as in FIG. 1A, FIG. 1B shows stent 107 on an expandable balloon 110. However, stent 107 could be a self-expanding stent, such that once positioned within a body lumen, it naturally expands.

In another example, U.S. Pat. No. 6,565,599 to Hong et al., the disclosure of which is incorporated herein by reference in its entirety, describes rows formed from sinusoidally shaped segments which are interconnected by elongated struts of a flexible polymer material, which hold the rows apart from one another. U.S. Pat. No. 6,475,237 to Drasler et al., the disclosure of which is incorporated herein by reference in its entirety, describes a strut wherein a portion thereof is made thinner and more flexible such that the strut can flex at those locations. However, the struts in these applications are formed as one piece. Thus, one portion of the strut cannot move independently of a separate portion of the strut. Further, these struts do not allow the strut rotational movement because each end of the strut is permanently coupled to adjacent rows.

Further, U.S. Pat. No. 5,035,706 to Gianturco, the disclosure of which is incorporated herein by reference in its entirety, describes the use of interlocking rings to connected adjacent segments. However, these interlocking rings, while providing improved flexibility over a strut, do not allow the segments to lay flat against the walls of the sides of the lumen. U.S. Pat. No. 6,387,122 to Cragg, the disclosure of which is incorporated herein by reference in its entirety, describes a helical stent in which subsequent windings are connected by loop members made from sutures, staple or rings of metal or plastic. Connecting rows of a helical stent, provides more contact between the stent and the lumen walls (i.e., more scaffolding) and thus provides better support for the lumen wall.

Thus, one object of stent design is to improve flexibility between adjacent rows, such as those formed by either cylindrical segments or helical windings, in order that the stent may move more easily through the tortuous body vessels to a treatment site.

BRIEF SUMMARY OF THE INVENTION

The present invention is directed to a stent having at least two rows, which are interconnected in various ways to increase the flexibility of the stent.

One aspect of the invention has interconnections between rows, which are divided into a first connecting portion and a second connecting portion. The first connecting portion has a first end, which is permanently and immovably coupled to a first row of a stent. The second connecting portion also has a first end that is coupled to a second row of the stent that is adjacent to the first row. Each of the first and second connecting portions has a second end that is interconnected with yet moves independently with respect to the second end of the other connecting portion.

The interconnections between the first and second rows may be in particular a ball and socket joint, a hinge joint or a universal joint. The ball and socket joint and the universal joint allow for movement between the connecting portions in any direction. A hinge joint may include a ball on the second end of the first connecting portion held by either a cuff or two loops on the second end of the second connecting portion.

In another aspect of the invention interlocking rings may connect adjacent rows. These rings lay flat against the lumen wall surface and may slide relative to one another.

The interconnections and/or rings described above provide a stent with additional flexibility for ease of implantation and maneuverability within a body lumen.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE FIGURES

The accompanying drawings, which are incorporated herein and form a part of the specification, illustrate the present invention and, together with the description, further serve to explain the principles of the invention and to enable a person skilled in the pertinent art to make and use the invention.

FIG. 7B is an alternative front plan view of the interconnection of FIG. 7A.

FIG. 7C is a perspective view of an embodiment of a component of the interconnection of FIGS. 7A and 7B.

FIG. 8 is a front plan view of interlocking rings between adjacent rows of a stent of the present invention.

FIG. 9 is a cross-section view along a line IX-IX of FIG. 8.

DETAILED DESCRIPTION OF THE INVENTION

Figure 1A:
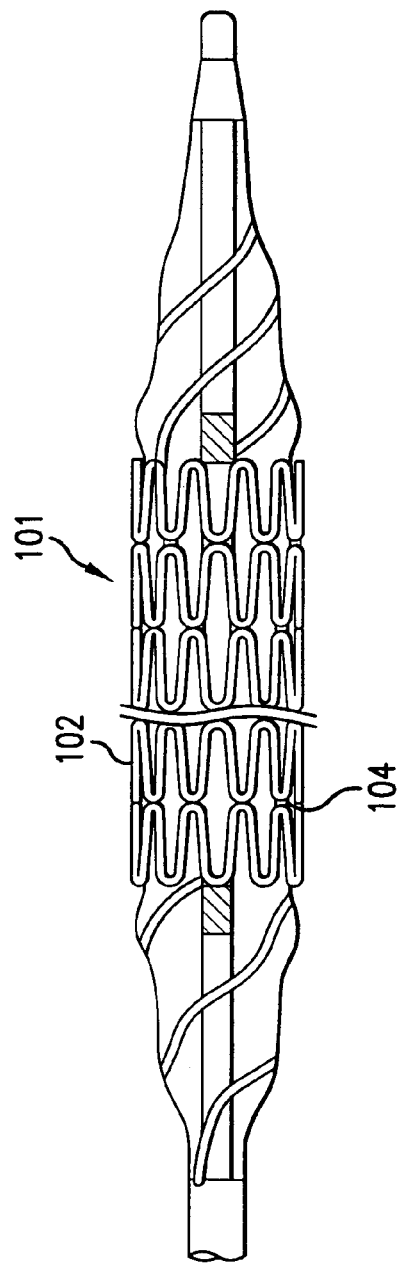
FIG. 1A is a front plan view of a prior art stent having rows formed from sinusoidally shaped cylindrical segments.

The present invention will be described with reference to the accompanying drawings. The drawing in which a feature first appears is typically indicated by the leftmost digit(s) in the corresponding reference number.

Figure 1B:
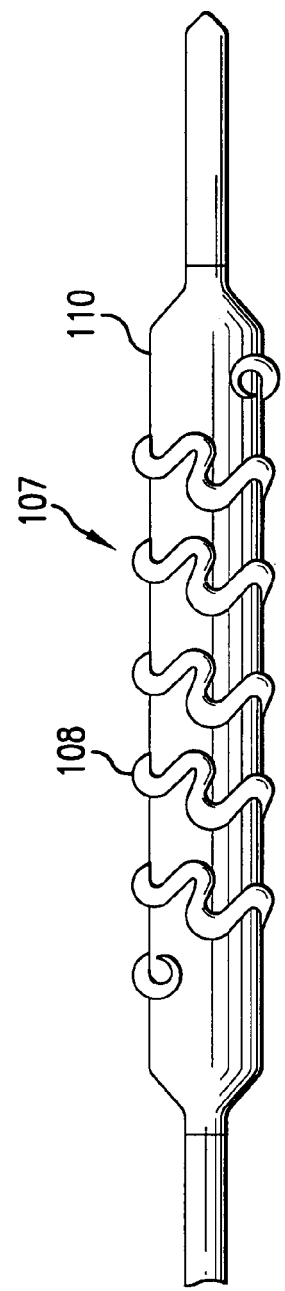
FIG. 1B is a front plan view of a prior art stent having rows formed from the helical windings of a sinusoidally shaped ribbon or wire.

FIGS. 1A and 1B show stents 101 and 107, respectively, in which the stent body comprises adjacent rows, which may be interconnected. In particular, the rows of stent 101 of FIG. 1A are separate cylindrical segments, which are interconnected by welding a first row directly to a second row, in this case at apexes 104 of sinusoidally shaped segments. FIG. 1B shows rows formed from helical windings 108, in this case of a sinusoidally shaped wire or ribbon. A stent of the present invention has adjacent rows, for example those shown in FIGS. 1A and 1B, with increased flexibility by using various ways of interconnecting adjacent rows. Although FIGS. 1A and 1B show rows that are sinusoidally shaped, the present invention contemplates stents having other overall generally cylindrical shaped stent bodies in which one portion thereof is interconnected to another portion thereof by means of a flexible interconnection, such as described in detail below. Although the examples discussed herein feature rows that are sinusoidally shaped, as the present invention is particularly suited to such stents, they are provided as examples only and are not intended to limit the scope of this invention.

The sinusoidal shapes of the stent bodies shown in FIGS. 1A and 1B comprise a series of peaks and valleys. For the purpose of this description, peaks and valleys may face either longitudinal direction provided that all peaks face one longitudinal direction and all valleys face the opposite longitudinal direction. For example, when two rows are side by side, flipping one row in the opposite direction would, by definition, convert all the peaks to valleys and valleys to peaks.

Each example shown herein includes sinusoidally shaped rows in which peaks and valleys are out of phase, i.e., the peaks of one row are facing the valleys of the adjacent rows and the adjacent rows are connected peak to valley. However, one skilled in the art can appreciate that adjacent sinusoidally shaped rows can be aligned such that peaks of one row face the peaks of an adjacent row and are connected peak to peak or valley to valley. Further, one skilled in the art can appreciate that the peaks of one row may also face a different part of the adjacent row than its peaks or valleys, and the rows may be interconnected by portions other than peaks or valleys.

Figure 2:
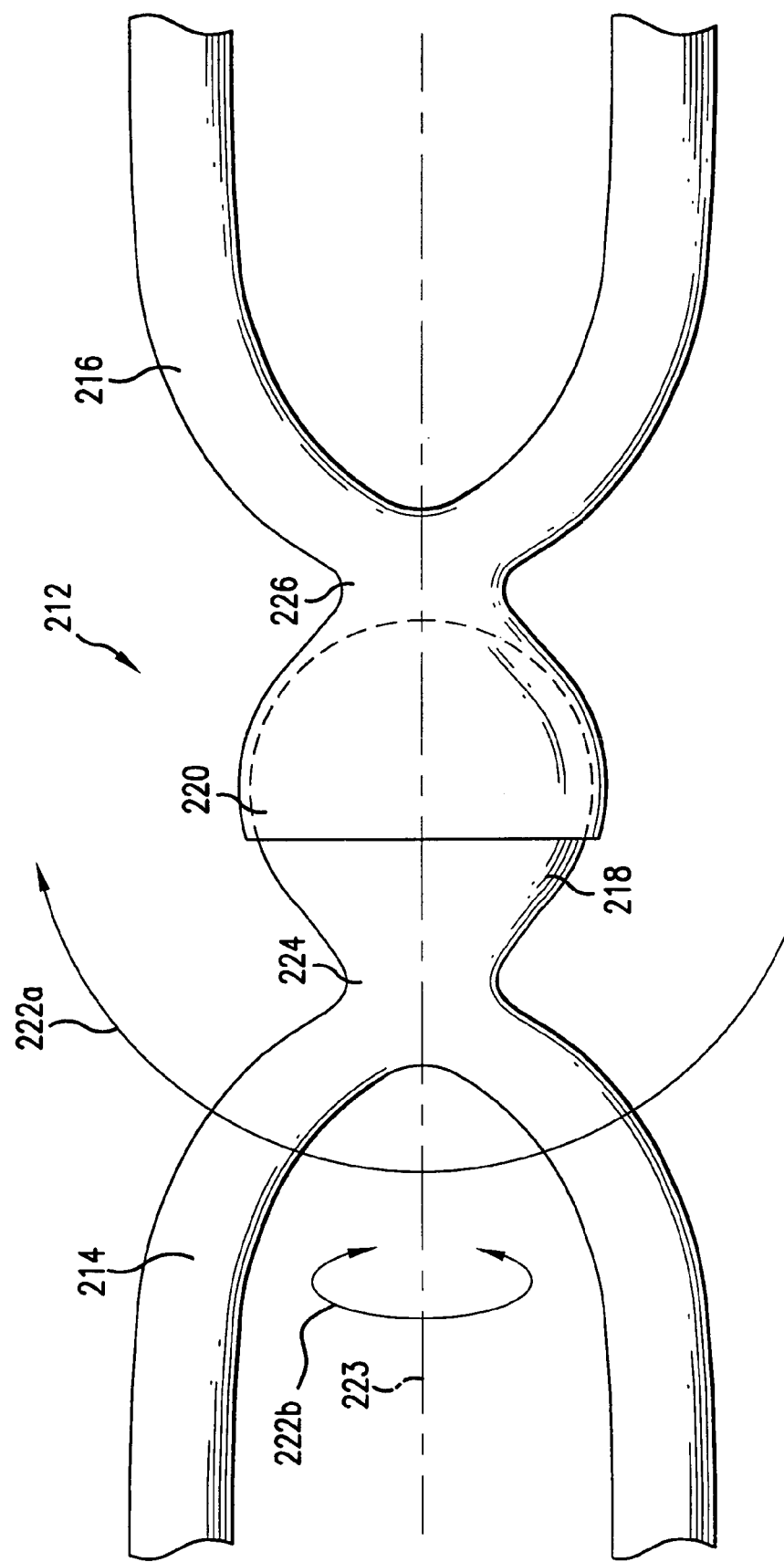
FIG. 2 is a front plan view of an interconnection between adjacent rows of a stent of the present invention.

FIG. 2 shows an interconnection 212 between adjacent rows of a stent of the present invention, shown between a peak 214 of one row and a valley 216 of an adjacent row, for example where the rows are sinusoidally shaped cylindrical segments or helical windings. The interconnection 212 shown in FIG. 2 is generally a ball and socket joint. The ball and socket joint includes a ball 218 and a socket 220.

Ball 218 may move freely within socket 220. In the embodiment shown in FIG. 2, socket 218 covers just over half of ball 218, thus providing peak 214 almost 180 degrees of movement, as suggested by arrow 222*a*. In fact, peak 214 can move radially almost 180 degrees not only in the direction marked by arrow 222*a*, but also in any direction around an axis 223, as illustrated by arrow 222*b*. Thus, a ball and socket joint, such as that shown in FIG. 2, provides great flexibility in movement between adjacent rows.

One skilled in the art can appreciate that other ball and socket joints in which the socket covers more of the ball, such that radial movement of peak 214 may be less than 180 degrees is contemplated by the present invention. However, it is preferred that the ball 218 be allowed maximum flexibility and movement with respect to socket 220. In addition, a ball and socket joint, such as that shown in FIG. 2, provides rotational movement of ball 218 within socket 220, such that peak 214 may rotated with respect to valley 216 about axis 223.

Ball 218 is permanently coupled to peak 214 by a neck 224, and socket 220 is permanently coupled to valley 216 by a neck 226. One skilled in the art can appreciate that, in an alternate embodiment, socket 220 may be coupled to peak 214 and ball 218 may be coupled to valley 216.

For embodiments that include sinusoidally shaped rows such as shown in FIGS. 1A and 1B, a ball and socket joint may connect a peak of one sinusoidally shaped row to a peak of an adjacent sinusoidally shaped row. Similarly, a valley may be connected to a valley. In these embodiments, necks 224 and 226 may be elongated to span the distance between different parts of adjacent rows.

Stents are generally formed using any of a number of different methods. Some stents may be formed by winding a wire around a mandrel, welding or otherwise forming the stent to a desired configuration, and finally compressing the stent to an unexpanded diameter. Other stents are manufactured by machining tubing or solid stock material into bands, and then deforming the bands to a desired configuration. Laser or chemical etching or another method of cutting a desired shape out of a solid stock material or tubing may be used to form other stents. Stent bodies are often made of stainless steel, platinum, cobalt based alloys (such as 605L and MP35N), titanium, tantalum, superelastic nickel-titanium alloy, other biocompatible metals or thermoplastic polymers.

In the present invention, interconnection 212 of FIG. 2 may be made from the same or different biocompatible material as that of the rows it connects together. Further, ball 218 may be formed or coated with a material that reduces friction between ball 218 and socket 220. Examples of suitable friction reducing materials include, but are not limited to, TEFLON coatings, TEFLON impregnation into one of the ball 218 or socket 220, hydrophilic compounds, temporary or permanent hydrogel coatings, polymers with a low coefficient of friction, such as parylene and polyvinyl pyrrolidone (PVP), and lipids, or other lubricious biocompatible materials as would be apparent to one skilled in the art. Interconnection 212 may be manufactured separately from the rows and later coupled thereto. For example, neck 224 may be formed by welding ball 218 to peak 214, such as by laser welding, resistance welding, friction welding or another type of welding as would be clear to one skilled in the art. The same may be true for forming neck 226 between socket 220 and valley 216. Ball 218 may also be formed as a unitary structure with peak 214, such as by the laser and/or chemical etching techniques discussed above, or by another method that would be apparent to one skilled in the art. Meanwhile, socket 220 may be formed as a unitary structure with valley 216, in a similar fashion. Thus, ball 218 and socket 220 are subsequently interlocked together to form movable interconnection 212. Alternatively, the ball 218 and socket 220 may be interlocked together before interconnection 212 is welded or otherwise attached to peak 214 and valley 216. Further, ball 218 and socket 220 may be formed interconnected, such as by etching, metal injection molding or another such method as would be apparent to one skilled in the art.

Figure 3:
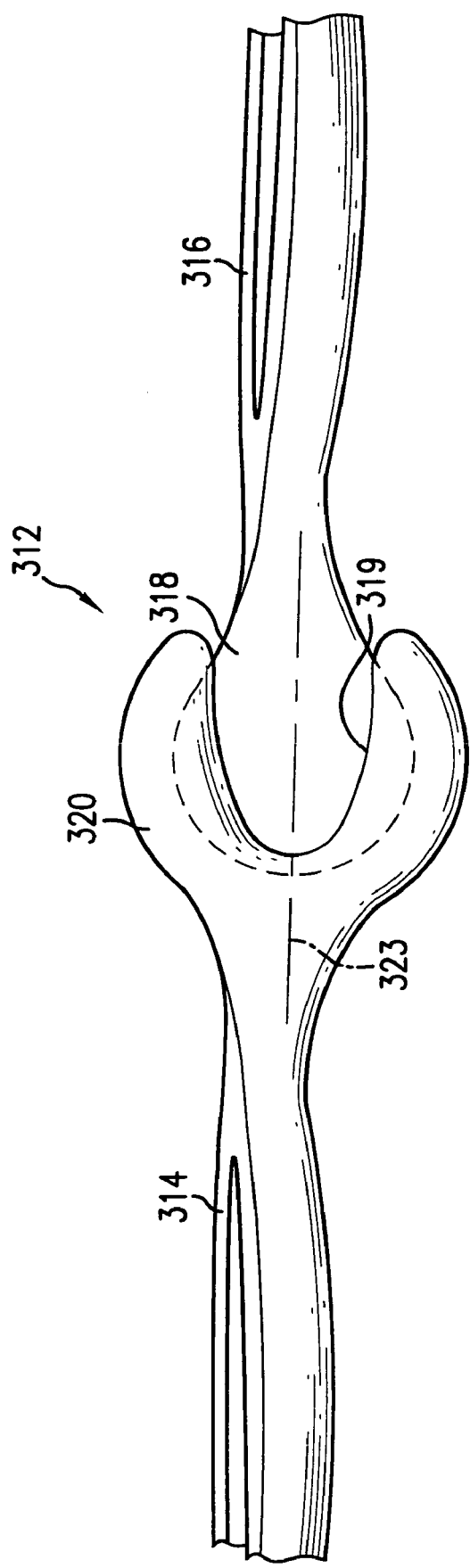
FIG. 3 is a side perspective view of an alternate interconnection between adjacent rows of a stent of the present invention.

FIG. 3 shows a side perspective view of another interconnection 312 between a peak 314 of one row and a valley 316 of an adjacent row. The interconnection 312 in this embodiment is a hinge joint, in which a ball 318 can only move one general direction within a cuff 320, along a track 319 that is formed by cuff 320. Thus, cuff 320 surrounds ball 318 limiting its motion to be generally in one plane, perpendicular to the orientation of the cuff 320.

Better flexibility can be achieved in the overall stent by alternating the directions of a hinge joint between each adjacent row. For example, a first hinge joint may allow for movement in a first direction between first and second rows and a second hinge joint, rotated 90 degrees from the first hinge joint, may allow for movement in a second direction between the second row and a third row. However, the rotational movements of adjacent interconnections may be offset by more or less than 90 degrees, depending upon the type of flexibility desired in any particular location along the longitudinal length of the stent. In addition, the degree to which the cuff surrounds the hinge may allow more or less flexibility and add more radial strength as necessary.

Valley 316 may be able to move greater than 180 degrees with respect to peak 314, depending upon how deeply the track 319 in cuff 320 is made. In addition, ball 318 provides rotational movement within cuff 320, such that valley 316 may be able to rotate with respect to peak 314 about an axis 323.

Figure 4A:
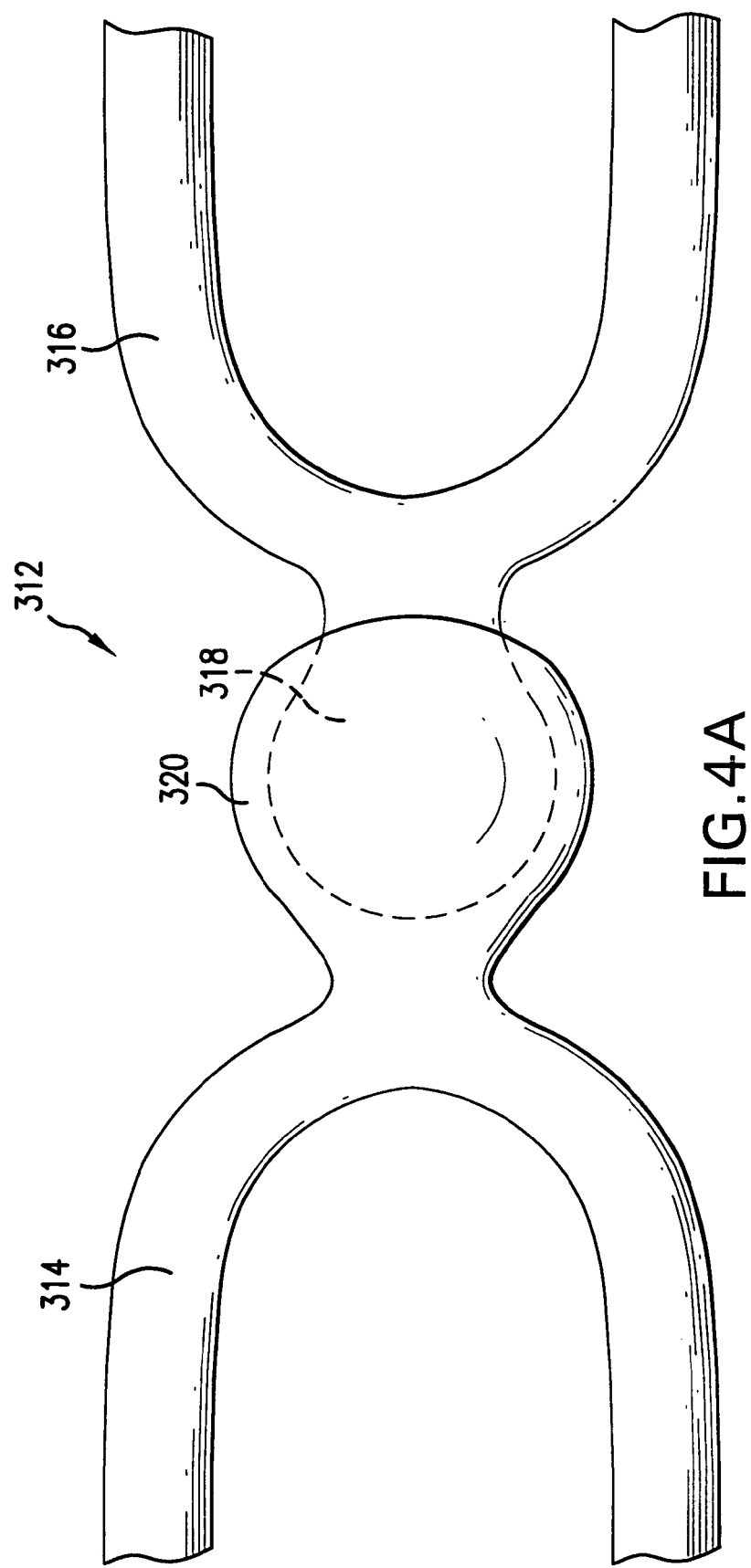
FIG. 4A is a front plan view of the interconnection of FIG. 3.
Figure 4B:
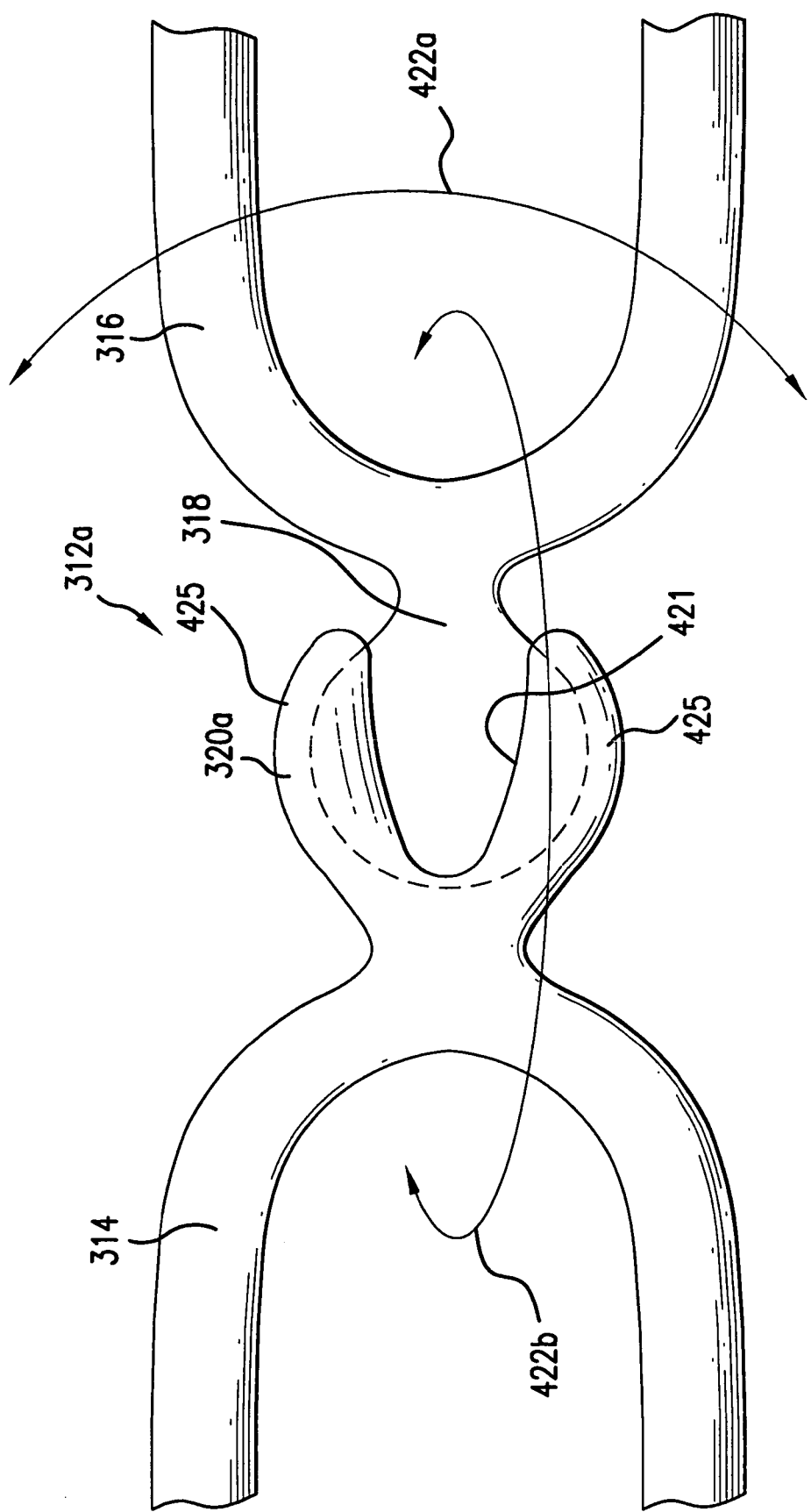
FIG. 4B is an alternative front plan view of the interconnection of FIG. 3.

FIG. 4A shows a frontal plan view of the interconnection 312 of FIG. 3, showing that cuff 320 surrounds ball 318 when viewed from the front, such that ball 318 stays securely therein, and the direction of movement of ball 318 with respect to cuff 320 is limited to one direction. FIG. 4B shows a front plan view of an alternative interconnection 312*a*. Interconnection 312*a* has the same side view as interconnection 312 shown in FIG. 3. Thus, interconnection 312*a* also includes a ball 318 disposed in a cuff 320*a*. However, cuff 320*a* includes a second track 321, such that ball 318 can move in a second direction with respect to cuff 320*a*. Cuff 320*a* has four prongs 325 which surround ball 318 and hold it into place. In FIG. 4B, arrow 422*a* shows the first direction that peak 314 can move with respect to valley 316 via track 319, and arrow 422*b* shows the second direction that peak 314 can move with respect to valley 316 via track 321. A stent of the present invention having the interconnection shown in FIGS. 3A and 4B may be manufactured in a manner similar to that described above with respect to FIG. 2.

Figure 5:
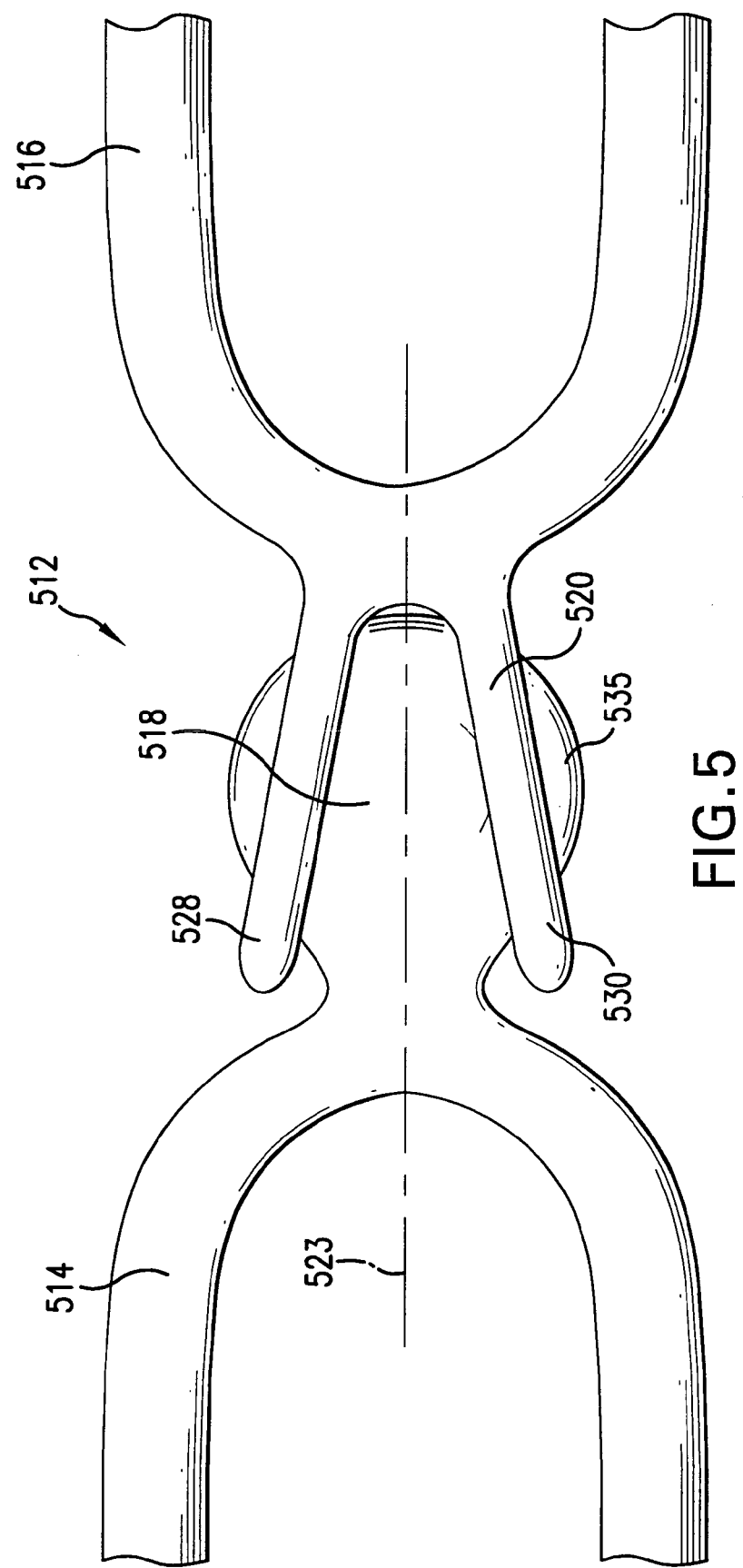
FIG. 5 is a front plan view of an alternate interconnection between adjacent rows of a stent of the present invention.

FIG. 5 shows another interconnection 512 between adjacent rows of a stent of the present invention. Interconnection 512 is also a hinge joint in that it allows a ball 518 to move only in one general direction. However, a socket 520 is formed from a first loop 528 and a second loop 530. Ball 518 rests between first loop 528 and second loop 530. First and second loops 528, 530 have a natural bias towards one another, such that ball 518 is held in place by pressure placed on the loops as the ball forces them apart. Tension may also be placed on the loops by an external force, such as a weld between the loops, an elastic loop composed of biocompatible materials or another biasing force as would be apparent to one skilled in the art.

Figure 6:
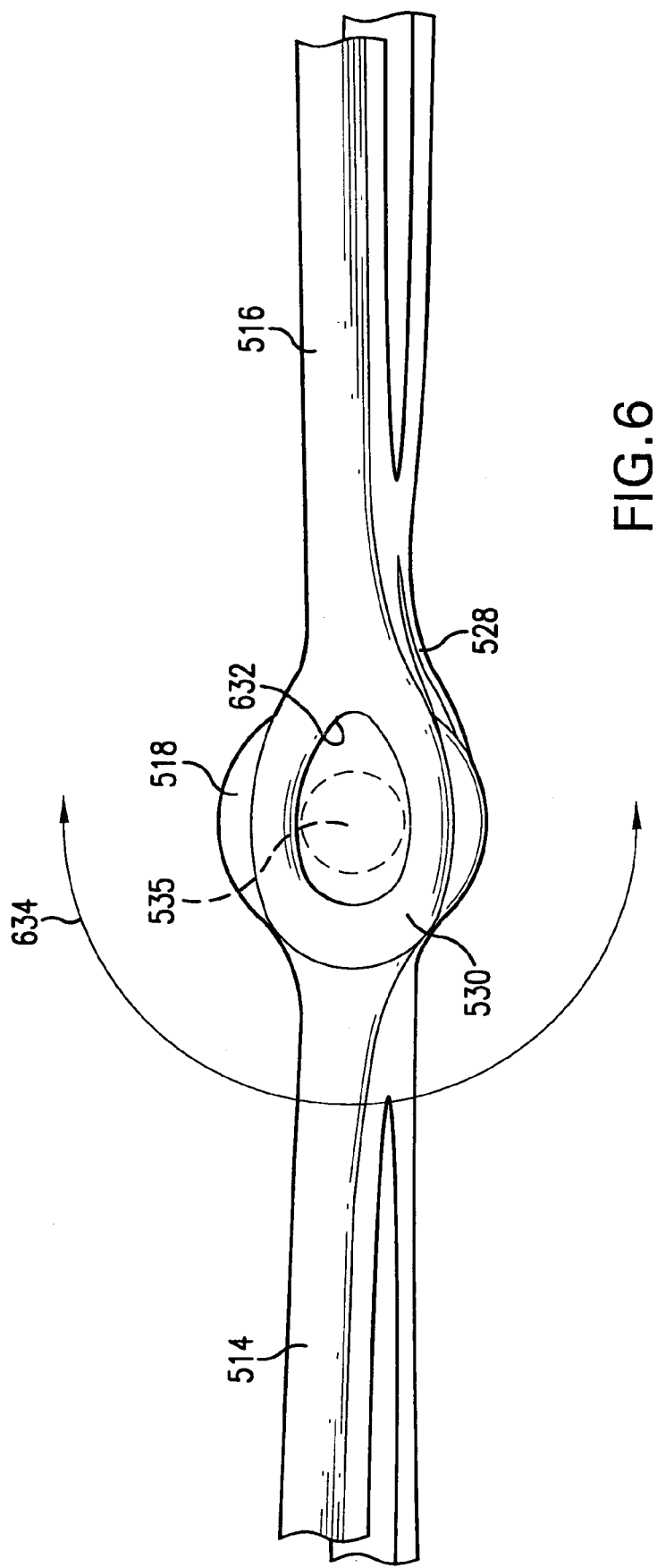
FIG. 6 is a side perspective view of the interconnection of FIG. 5.

FIG. 6 shows a side perspective view of the interconnection 512 of FIG. 5. FIG. 6 shows loops 528, 530 with holes 632 to keep ball 518 in place while allowing peak 514 to move in the plane shown by the double arrow 634. A portion 535 of ball 518 fits through both of loops 528, 530 to keep ball 518 securely held in the socket formed by the two loops 528, 530, but still allows ball 518 to move within the socket. Ball 518 also may have rotational movement within loops 528, 530, such that peak 514 may rotate with respect to valley 516 about an axis 523. In addition, the size of the loops may be increased or decreased in order to facilitate movement in the plane perpendicular to the holes in the loops.

As discussed above with respect to FIGS. 3 and 4, flexibility of the overall stent can be improved by alternating the directions of a first hinge joint of FIG. 5 between a first and second row and a second hinge joint between a second and third row. Further, interconnection 512 can be manufactured according to any of the methods discussed above with respect to FIG. 2.

Figure 7A:
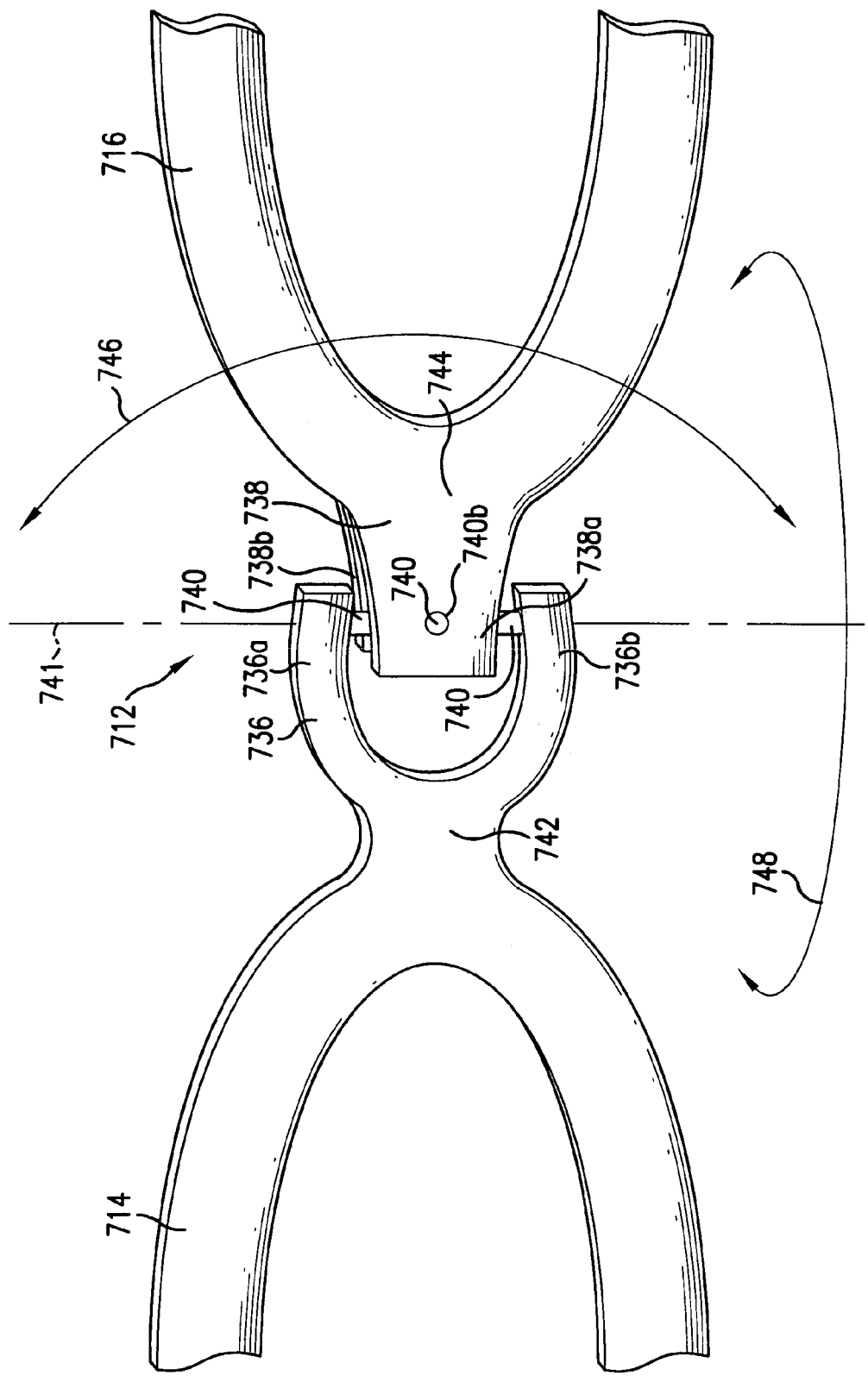
FIG. 7A is a front plan view of an alternate interconnection between adjacent rows of a stent of the present invention.

FIG. 7A shows a front plan view of another interconnection 712 between adjacent rows of a stent of the present invention. Interconnection 712 is a universal joint including a first U-shaped member 736, which has the "U" opening in a first direction, a second U-shaped member 738, which has the "U" opening in a second direction opposite to the first direction and facing towards first U-shaped member 736. First U-shaped member 736 is rotated 90 degrees from second U-shaped member 738. FIG. 7B is an alternative view of interconnection 712, wherein valley 716 is rotated 90 degrees from the position shown in FIG. 7A about an axis 741. As seen in FIG. 7B, interconnection 712 has a plus-shaped (+) member 740 having a first end 740a, a second end 740b, a third end 740c and a fourth end 740d, which are rotatably attached to first and second U-shaped members 736 and 738. In particular, first end 740a and third end 740c are rotatably connected to opposite ends 736a and 736b of first U-shaped member 736, and second end 740b and fourth end 740d are rotatably connected to a opposite ends 738a and 738b of U-shaped member 738. Further, a curved portion 742 of U-shaped member 736 is coupled to peak 714, and a curved portion 744 is coupled to valley 716.

One way of forming the universal joint of interconnection 712 may include the development of a two-piece plus shaped member 740, as shown in FIG. 7C, having a first arm 780 and a second arm 782. First arm 780 includes an opening 784 similar to the eye of a needle and is attached to U-shaped member 736 by opening opposite ends 736a and 736b to fit first arm 780 into place. Subsequently, second arm 782, which is a press fit pin, is slid through a bore, shown in FIG. 7A, in end 738a of U-shaped member 738, through opening 784 of first arm 780 and through end 738b of U-shaped member 738. The plus shaped member 740 may or may not be secured into position, such as by welding first arm 780 to second arm 782, depending upon the security of the press fit. Alternatively, plus shaped member 740 may be formed as one-piece and inserted by opening opposite ends of both U-shaped members 736 and 738. U-shaped members 736 and 738 may be formed as a unitary structure with peak 714 and valley 716, respectively. Alternatively, interconnection 712, including U-shaped members 736 and 738, may be assembled and subsequently welded to peak 714 and valley 716.

Thus, peak 714 and valley 716 may move with respect to one another in two dimensions as shown by arrows 746 and 748 of FIG. 7A. In particular, peak 714 can move in the direction of arrow 748, while valley 716 can move in the direction of arrow 746, as shown in FIG. 7B by the 90 degree rotation of valley 716.

Customized flexibility can be achieved by alternating the directions of interconnection 712 between subsequent adjacent rows. For example, a first row may be connected to a second row using a first interconnection 712 as shown in FIGS. 7A and 7B. Meanwhile, the second row may be connected to a third row, by a second interconnection 712 that is rotated, for example, 45 degrees, from first interconnection 712.

FIG. 8 shows interlocking rings 850 that interconnect adjacent rows of a stent of the present invention. In particular, FIG. 8 shows a first ring 852 and a second ring 854. In the embodiment of FIG. 8, first ring 852 is coupled to a peak 814 of a first sinusoidally shaped row at a neck 824, and second ring 854 is coupled to a valley 816 of a second sinusoidally shaped row at a neck 826.

Generally interlocking rings do not lay flat against a lumen wall because a portion of one ring abuts a portion of the other ring. However, interlocking rings 850 of FIG. 8 solve this problem. In particular, FIG. 9 shows a cross section taken along line IX-IX of FIG. 8. FIG. 9 shows where first ring 852 interlocks with second ring 854. First ring 852 has a first side 856 and a second side 958. First ring has a first indentation 860 formed into first side 856 and a second indentation 962 formed into second side 958. Similarly, second ring 854 has a first side 864 and a second side 966. Second ring 854 has a third indentation 868 formed into first side 864 and a fourth indentation 970 formed into second side 966. As the rings are interlocked, first indentation 860 of first ring 852 is recessed into fourth indentation 970 of second ring 854, and second indentation 962 of first ring 852 is recessed into third indentation 868 of second ring 854.

Preferably, indentations are formed into each of first and second rings 852 and 854 to a depth 972 which is about half of the overall height 974 of the first and second rings 852, 854. Thus, when interlocked, the overall height 974 of the interlocking rings does not change. Thus, the interlocking rings lay flat against a lumen wall.

Each of the indentations is elongated and somewhat arcuate shaped around the curve of first and second rings 852/854, as seen in FIG. 8. Thus, the indentations create a track along which the corresponding indentation may move. Thus, the interlocking rings can be shifted in a variety of directions, without increasing the overall height 974 of the stent. For example, peak 814 may be shifted towards or away from valley 816, and valley 816 may be moved in the direction of arrow 876 with respect to peak 814, while still remaining flat against the wall of the body lumen. Any of the indentations may be coated with a material to reduce the friction between the sliding interlocking rings 850.

Any number of interconnections or interlocking rings described herein may be placed between adjacent rows of a stent of the present invention. For example, with sinusoidally shaped rows, if there are N number of peaks on a first sinusoidally shaped row, there may be between one and N interconnections or interlocking rings between the first sinusoidally shaped row and an adjacent second sinusoidally shaped row. Further, the number of interconnections or interlocking rings between a first and an adjacent second row may be different than the number of interconnections or interlocked rings between the second and an adjacent third row.

While the invention has been particularly shown and described with reference to preferred embodiments thereof, it will be understood by those skilled in the art that they have been presented by way of example only, and not limitation, and various changes in form and details can be made therein without departing from the spirit and scope of the invention. For example, each of the embodiments described in the figures shows a peak connected to a valley of sinusoidally shaped rows. However, each of the interconnections and interlocking rings described herein may connect any type of adjacent row of a stent in a variety of ways.

Thus, the breadth and scope of the present invention should not be limited by any of the above-described exemplary embodiments, but should be defined only in accordance with the following claims and their equivalents. Additionally, all references cited herein, including issued U.S. patents, or any other references, are each entirely incorporated by reference herein, including all data, tables, figures, and text presented in the cited references.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A flexible stent comprising:
   a first row;
   a second row adjacent said first row; and
   an interconnection between said first and second rows when the stent is collapsed to an insertion diameter, wherein said interconnection includes a first connecting portion and a second connecting portion interlocked with said first connecting portion, said first connecting portion having independent movement with respect to said second connecting portion,
   wherein said first connecting portion has a first end and a second end, said first end permanently coupled to said first row, and wherein said second connecting portion has a first end and a second end, said first end of said second connecting portion being permanently coupled to said second row, wherein said second ends of said first and second connecting portions form the interlocked connection with independent movement.

2. The flexible stent of claim 1, wherein said first ends of said first and second connecting portions are coupled to said first and second rows, respectively, via laser welding, resistance welding or friction welding.

3. The flexible stent of claim 1, wherein said first connecting portion is formed as a unitary structure with said first row and said second connecting portion is formed as a unitary structure with said second adjacent row.

4. The flexible stent of claim 1, wherein said rows are formed by cylindrical segments.

5. The flexible stent of claim 1, wherein said rows are formed by the windings of a helical stent body.

6. The flexible stent of claim 1, wherein said first connecting portion is a ball and a second connecting portion is a socket, such that said interconnection is a ball and socket joint.

7. The flexible stent of claim 1, wherein said interconnection is a hinge joint.

8. The flexible stent of claim 7, wherein a first hinge joint between said first and second rows allows movement in a first direction and a second hinge joint between said second row and a third row allows movement in a second direction, which is different from said first direction.

9. The flexible stent of claim 7, wherein said first connecting portion is a ball and a second connecting portion is a cuff.

10. A flexible stent comprising:
    a first row;
    a second row adjacent said first row; and
    an interconnection between said first and second rows, wherein said interconnection includes a first connecting portion and a second connecting portion interlocked with said first connecting portion, said first connecting portion having independent movement with respect to said second connecting portion, wherein said first connecting portion is a ball and a second connecting portion comprises two loops, wherein said ball is held in place between said loops by projecting into holes formed in said loops.

11. The flexible stent of claim 1, wherein said interconnection is a universal joint.

12. A flexible stent comprising:
    a first row;
    a second row adjacent said first row; and
    an interconnection between said first and second rows, wherein said interconnection includes a first connecting portion and a second connecting portion interlocked with said first connecting portion, said first connecting portion having independent movement with respect to said second connecting portion, wherein said first connecting portion is a first U-shaped member, said second connecting portion is a second U-shaped member, and said interconnection further comprises a plus shaped member rotatably connecting said first U-shaped member to said second U-shaped member.

13. The flexible stent of claim 12, wherein said plus shaped member is a two piece assembly.

14. The flexible stent of claim 1, wherein said interconnection provides rotational movement of one of said first connecting portion and said second connecting portion with respect to the other of said first connecting portion and said second connecting portion.

15. The flexible stent of claim 1, wherein said first and second rows are formed from a material selected from the group consisting of stainless steel, platinum, cobalt based alloys, titanium, tantalum, superelastic nickel-titanium alloy, and thermoplastic polymers.

16. The flexible stent of claim 15, wherein said first and second connection portions are the same material as the first and second rows.

17. The flexible stent of claim 15, wherein at least one of said first and second connection portions are a different material than first and second rows.

18. The flexible stent of claim 1, wherein at least one of said first and second connection portions is coated with a material to reduce friction between said first and second connection portions.

19. The flexible stent of claim 1, wherein said first and second rows are sinusoidally shaped.

20. An flexible stent device comprising:
a first row;
a second row adjacent said first row;
a pair of interlocking rings between said first and second rows, wherein said pair of interlocking rings comprise a first ring permanently coupled to said first row and a second ring permanently coupled to said second row, wherein each of said first and second rings has a first indentation and a second indentation for receiving the first and second indentations of the other of said first and second rings, such that when interlocked, said rings will lay flat against a body lumen wall.

21. The flexible stent of claim 20, wherein said first and second indentations form a track along which the other of said first and second rings can move and still lay flat.

22. The flexible stent of claim 20, wherein said first and second indentations of each of said first and second rings has a depth about half of the overall height of said first and second rings.

23. The flexible stent of claim 20, wherein said first and second indentations of at least one of said first and second rings is coated with a material to reduce friction between said first and second rings.

* * * * *